(12) United States Patent
Osypka

(10) Patent No.: US 8,670,843 B2
(45) Date of Patent: Mar. 11, 2014

(54) QUADRIPOLAR CONNECTOR ASSEMBLY FOR ACTIVE FIXATION CARDIAC LEADS

(75) Inventor: Thomas P. Osypka, Palm Harbor, FL (US)

(73) Assignee: Oscor Inc., Palm Harbor, FL (US)

( * ) Notice: Subject to any disclaimer, the term of this patent is extended or adjusted under 35 U.S.C. 154(b) by 119 days.

(21) Appl. No.: 13/443,034

(22) Filed: Apr. 10, 2012

(65) Prior Publication Data
US 2012/0265281 A1    Oct. 18, 2012

Related U.S. Application Data

(60) Provisional application No. 61/516,991, filed on Apr. 12, 2011.

(51) Int. Cl.
*A61N 1/372* (2006.01)
(52) U.S. Cl.
USPC ............ 607/127; 607/119; 607/122; 607/126
(58) Field of Classification Search
USPC .......................... 607/116, 119, 122, 126, 127
See application file for complete search history.

(56) References Cited

U.S. PATENT DOCUMENTS

2007/0299493 A1*  12/2007  Osypka ..................... 607/127
2010/0100164 A1*  4/2010  Johnson et al. ............ 607/116

* cited by examiner

*Primary Examiner* — Joseph Dietrich
(74) *Attorney, Agent, or Firm* — Edwards Wildman Palmer LLP; Scott D. Wofsy

(57) ABSTRACT

An implantable active fixation cardiac lead is disclosed that includes an elongated lead body having opposed proximal and distal end portions and having an interior lumen extending therethrough, an axially rotatable extendable and retractable fixation helix operatively associated with the distal end portion of the lead body, a rotatable in-line quadripolar connector assembly operatively associated with the proximal end portion of the lead body and including an elongated rotatable pin electrode having opposed proximal and distal end portions, and an elongated torque transmitting conductor coil extending through the interior lumen of the lead body and having a proximal end portion connected to the distal end portion of the rotatable pin electrode and a distal end portion connected to the rotatable fixation helix, to facilitate manual activation of the fixation helix.

18 Claims, 5 Drawing Sheets

QUADRIPOLAR CONNECTOR ASSEMBLY FOR ACTIVE FIXATION CARDIAC LEADS

CROSS-REFERENCE TO RELATED APPLICATION

The subject application claims the benefit of priority from U.S. Provisional Patent Application Ser. No. 61/516,991 filed Apr. 12, 2011, the disclosure of which is herein incorporated by reference in its entirety.

BACKGROUND OF THE INVENTION

1. Field of the Invention

The subject invention is directed generally to implantable endocardial leads, and more particularly, to an active fixation cardiac lead having a quadripolar connector assembly with a rotatable pin electrode for manually activating the fixation helix at the distal end of the lead.

2. Background of the Related Art

Current implantable active fixation leads are designed with an extendable and retractable fixation helix or screw that can be retracted for transvenous insertion of the lead into the right atrium and ventricle and then extended so that the lead can be actively screwed into the endocardial wall. These are often configured as direct drive leads in which the fixation helix or screw can be extended or retracted by a stylet shaped with a screwdriver tip. An example of an active fixation lead which utilizes a screwdriver tipped stylet is the Physique® cardiac pacing lead manufactured by Oscor Inc. of Palm Harbor, Fla.

It is also known to link the electrode pin of the lead connector assembly of a cardiac lead to the fixation helix of the lead by way of a torque transmitting inner conductor coil. An example of an active fixation lead having an inner torque transmitting coil for activating a fixation helix by way of a rotatable connector pin is disclosed in commonly assigned U.S. Pat. No. 8,150,536 to Osypka, the disclosure of which is incorporated herein by reference in its entirety for purposes of enablement.

Active fixation quadripolar cardiac leads for pacing and/or defibrillation, such as those having IS-4 type in-line connectors, are also known in the art and have been disclosed for example in commonly assigned U.S. Pat. Nos. 7,585,190, 7,422,487 and 8,145,315 to Osypka, the disclosures of which are all herein incorporated by reference in their entireties for purposes of enablement. IS-4 type in-line connectors are configured in accordance with the ISO standard for four-pole (quadripolar) connector systems (PAC/CTF-N151R3) developed by the Connector Task Force (CTF) of the AAMI Pacemaker Committee, which is incorporated by reference herein in its entirety.

It would be beneficial to provide an implantable quadripolar cardiac lead with an IS-4 type connector assembly for manually activating the fixation helix located at the distal end of the lead by way of a torque transmitting conductor coil extending through the lead body.

SUMMARY OF THE INVENTION

The subject invention is directed to a new and useful implantable active fixation cardiac lead that includes, among other things, an elongated lead body having opposed proximal and distal end portions and an interior lumen extending therethrough. An axially rotatable extendable and retractable, electrically active fixation helix, and three axially spaced apart ring electrodes, are operatively associated with the distal end portion of the lead body. An in-line quadripolar connector assembly is operatively associated with the proximal end portion of the lead body. The connector assembly includes an elongated rotatable pin electrode having opposed proximal and distal end portions.

The cardiac lead of the subject invention further includes an elongated torque transmitting conductor coil that extends through the interior lumen of the lead body. The torque transmitting conductor coil has a proximal end portion connected to the distal end portion of the rotatable pin electrode and a distal end portion connected to the rotatable fixation helix, to facilitate manual activation of the fixation helix.

The in-line quadripolar connector assembly also includes an elongated inner support shaft for supporting a stack of axially spaced apart electrode rings separated from one another by a corresponding plurality of axially spaced apart insulator rings. The proximal-most insulator ring of the connector assembly is threadably engaged with a proximal end portion of the inner support shaft. A cylindrical hull is secured to the distal end portion of the pin electrode and it resides within a recess of the inner support shaft, proximal to the connection of the pin electrode and torque transmitting conductor coil, to act as a bearing for supporting rotation of the pin electrode within a central bore of the support shaft. A clearance gap is provided between the outer diameter of the hull and the inner diameter of the recess to allow free rotation of the hull relative to the support shaft.

The elongated support shaft includes three circumferentially spaced apart side channels. Each side channel is adapted and configured to accommodate a set of conductive wires that connect the axially spaced apart electrode rings of the in-line quadripolar connector assembly with axially spaced apart ring electrodes associated with the distal end portion of the lead body.

These and other features of the implantable quadripolar cardiac lead of the subject invention will become more readily apparent to those having ordinary skill in the art from the following detailed description of the preferred embodiments taken in conjunction with the drawings.

BRIEF DESCRIPTION OF THE DRAWINGS

So that those having ordinary skill in the art to which the subject invention pertains will more readily understand how to make and use the cardiac lead of the subject invention, preferred embodiments thereof will be described hereinbelow with reference to the drawings, wherein.

DETAILED DESCRIPTION OF THE PREFERRED EMBODIMENTS

Figure 1:
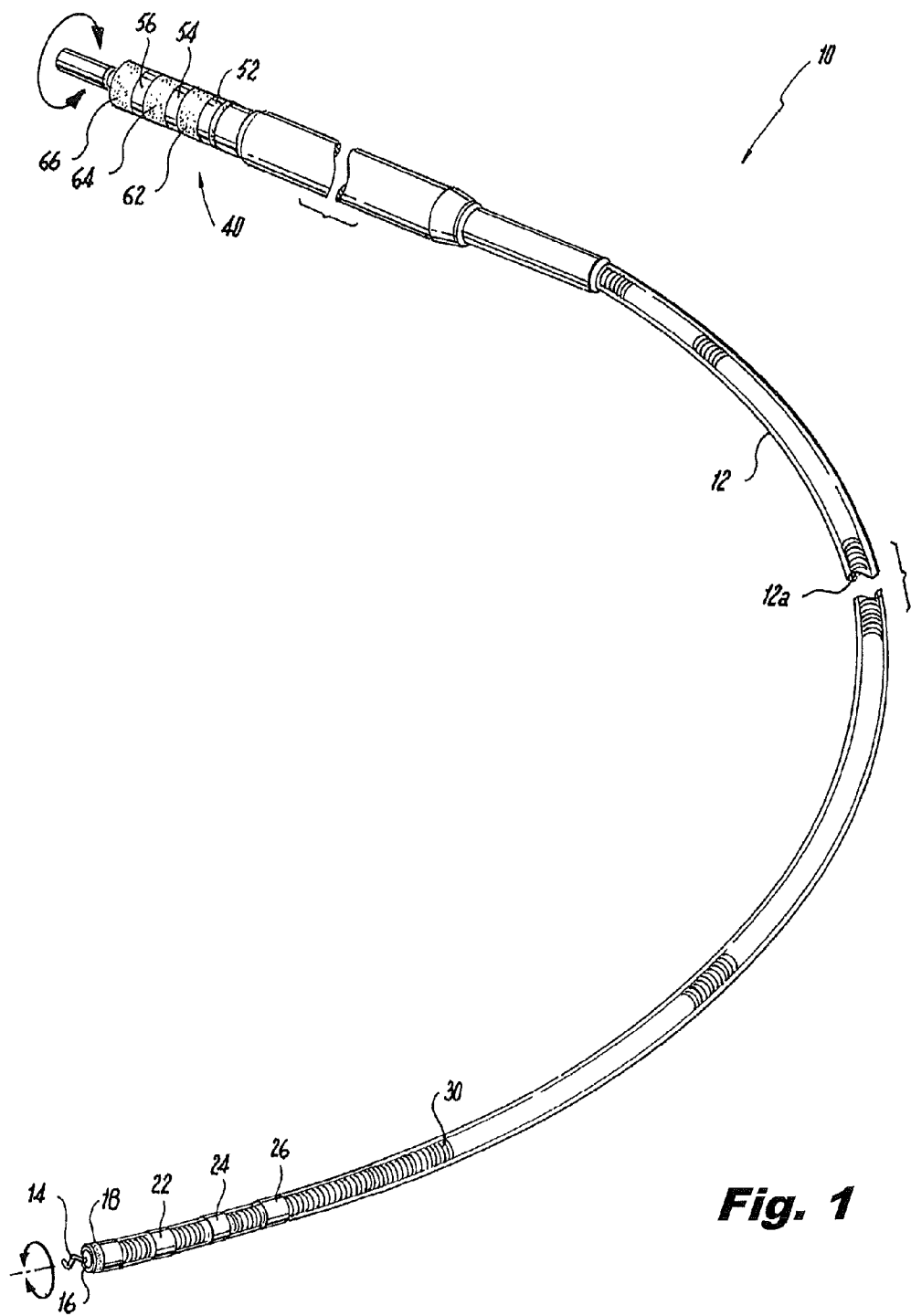
FIG. 1 is a perspective view of an implantable cardiac lead constructed in accordance with a preferred embodiment of the subject invention, which has an electrically active fixation helix and three axially spaced apart ring electrodes operatively associated with the distal end portion thereof, and an in-line quadripolar connector assembly operatively associated with the proximal end portion thereof.

Referring now to the drawings wherein like reference numerals identify similar structural elements or features of the subject invention, there is illustrated in FIG. 1 an implantable cardiac lead 10 configured for active fixation in cardiac tissue to facilitate atrial or ventricular cardiac pacing, sensing and/or defibrillation. The cardiac lead 10 of the subject invention includes an elongated flexible lead body 12, which is preferably formed from polyurethane or a similar biocompatible material such as silicone. The lead body preferably has an operative length of about between 48 cm and 58 cm and a diameter of about between 5 F and 7 F. The length and diameter of the lead could vary depending upon intended use or application.

The distal end portion of cardiac lead 10 includes an electrically active helical fixation screw 14 that is mounted for axial rotation relative to the distal end or tip 16 of lead body 12. The fixation screw 14 can be formed at least in part from stainless steel or an alloy of platinum and iridium, and is preferably about 1.5 mm in length. The helical configuration of fixation screw 14 allows for easy fixation in the myocardium.

The annular tip 16 of lead body 12 preferably defines an electrically active surface, which together with the electrically active fixation screw 14, defines a tip electrode of the quadripolar lead 10. The distal end portion of cardiac lead 10 further includes three axially spaced apart ring electrodes for pacing and/or sensing. These include a distal ring electrode 22, a medial ring electrode 24 and a proximal ring electrode 26. The three ring electrodes, together with the electrically active fixation screw provide a medical practitioner a wider range of flexibility for managing treatment than provided by unipolar or bipolar cardiac leads.

Those skilled in the art will readily appreciate that the arrangement of axially spaced apart ring electrodes on the distal end portion of the lead body 12 is merely an example of a particular electrode arrangement. It is not intended to limit the scope of the subject invention in any way. Indeed, alternative arrangements of electrodes can also be employed, without departing from the spirit of scope of the subject disclosure, including, for example, arrangements that also or otherwise utilize one or more shocking coils for defibrillation, an example of which is disclosed in commonly assigned U.S. Pat. No. 7,467,017 to Osypka, the disclosure of which is herein incorporated by reference in its entirety for purposes of enablement.

With continuing reference to FIG. 1, it is also envisioned that the distal end portion of lead body 12 could be configured with a steroid eluting ring 18, which would be located proximal to the tip electrode, to treat heart tissue at the implantation site of the fixation screw 14, as disclosed for example in commonly assigned U.S. Pat. No. 7,187,980 to Osypka, the disclosure of which is herein incorporated by reference in its entirety for purposes of enablement.

An elongated torque transmitting conductor coil 30 extends through an interior lumen 12a of the lead body 12 and is preferably covered by a heat shrink tube or similar insulating material, as discussed in more detail below with respect to FIGS. 2 and 3. Conductor coil 30 is operatively connected to the fixation screw 14 in such a manner so that axial rotation of the conductor coil 30 in a clock-wise or counter-clock wise direction relative to the axis of the lead body 12 effectuates corresponding axial rotation of the fixation screw 14, so as to extend and retract the fixation screw. More particularly, the fixation screw 14 is retracted during the transvenous insertion of the lead and then extended so that the lead can be actively screwed into the endocardial wall.

The torque transmitting coil 30 is preferably a multifilar conductor coil, as disclosed for example in commonly assigned U.S. Pat. No. 6,978,185 to Osypka, which is incorporated herein by reference in its entirety for purposes of enablement. An effective way to operatively connect the distal end portion of conductor coil 30 to fixation screw 14 is disclosed, for example, in FIG. 9E of commonly assigned U.S. Pat. No. 7,158,837 to Osypka et al., which is also incorporated herein by reference in its entirety for purposes of enablement.

Figure 2:
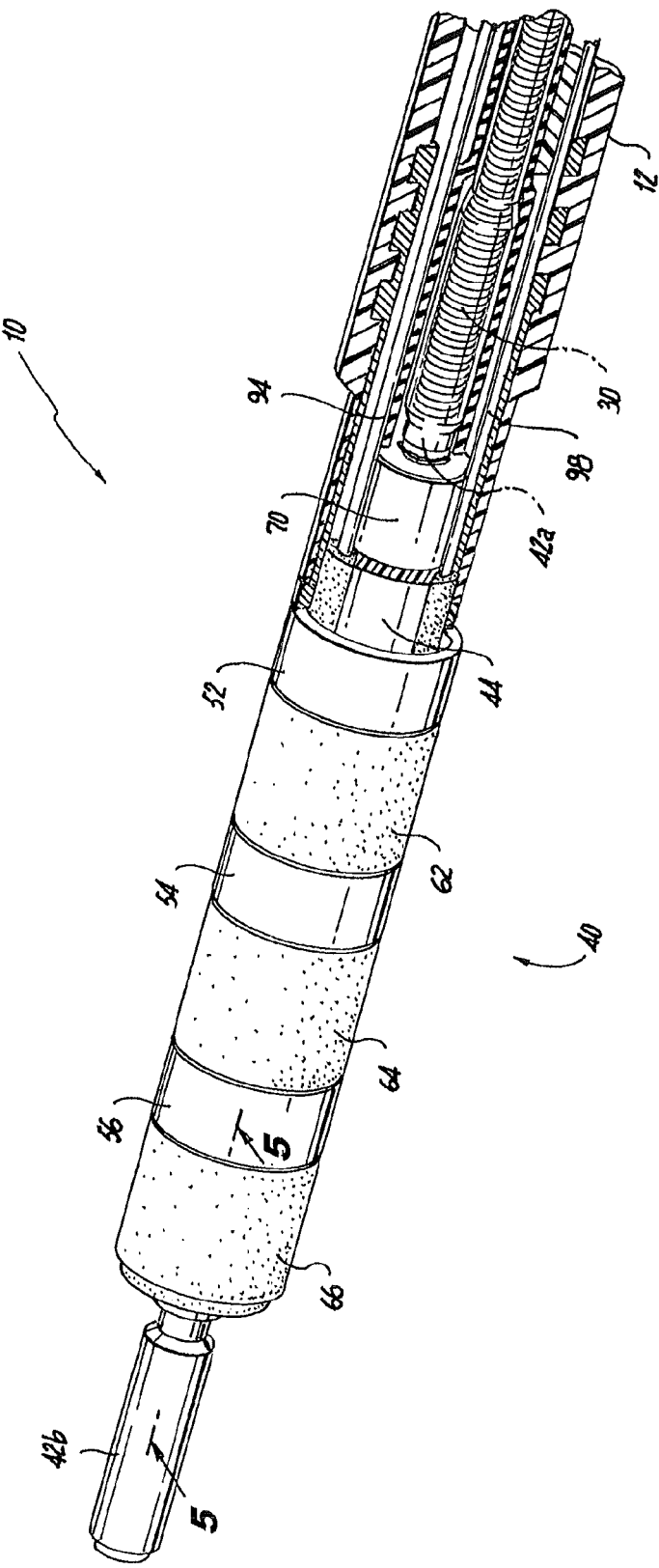
FIG. 2 is a perspective view of the in-line quadripolar connector assembly associated with the proximal end portion of the cardiac lead of FIG. 1, with the lead body in cross-section to show the connection between the distal end portion of the pin electrode of the connector assembly and the proximal end portion of the torque transmitting coil that extends to the fixation helix at the distal end of the lead.
Figure 3:
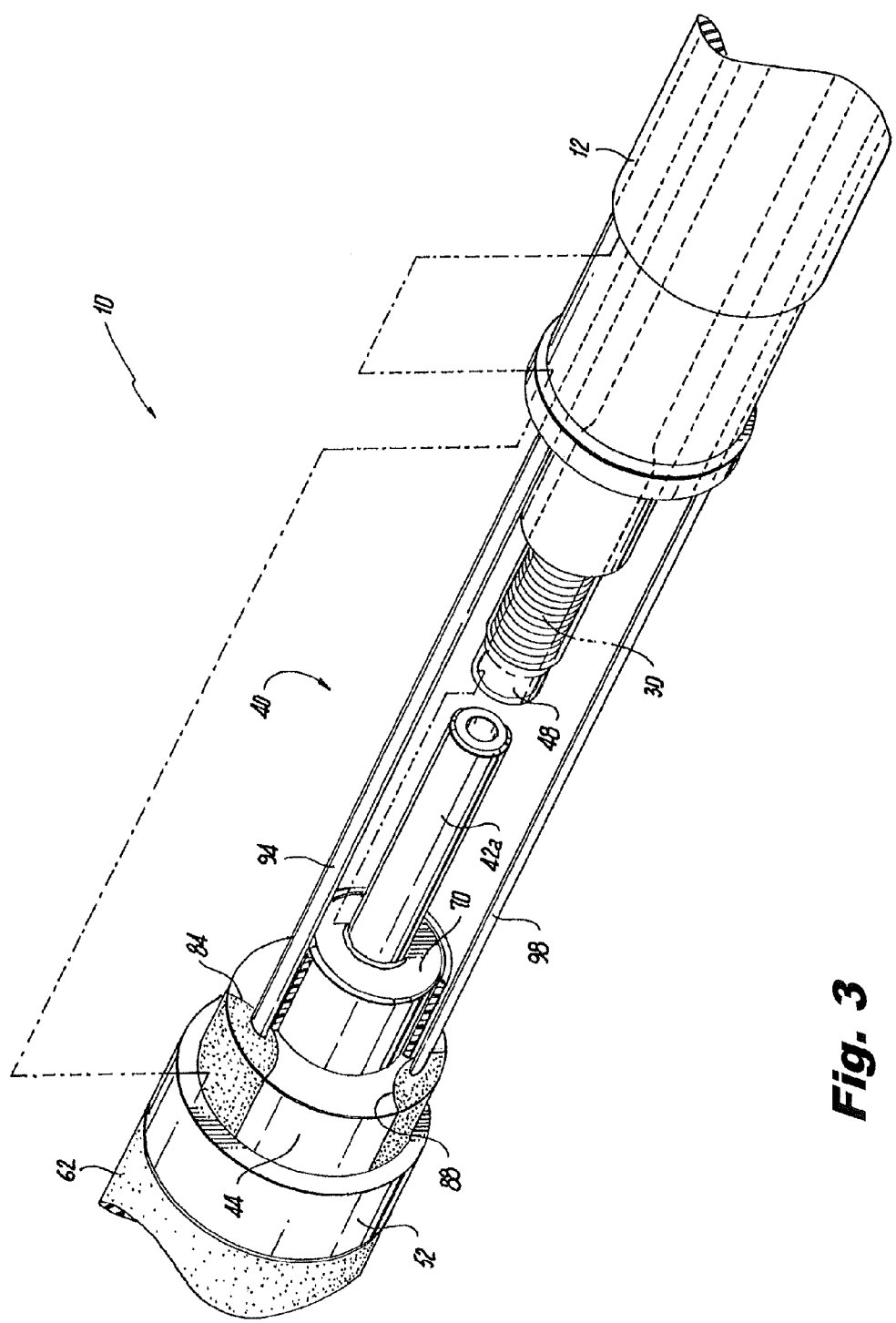
FIG. 3 is an exploded perspective view of a portion of the connector assembly, showing the connection between the distal end portion of the pin electrode and the proximal end portion of the shrink tube covered torque transmitting coil, adjacent to the cylindrical hull secured to the distal end portion of the pin electrode.
Figure 4:
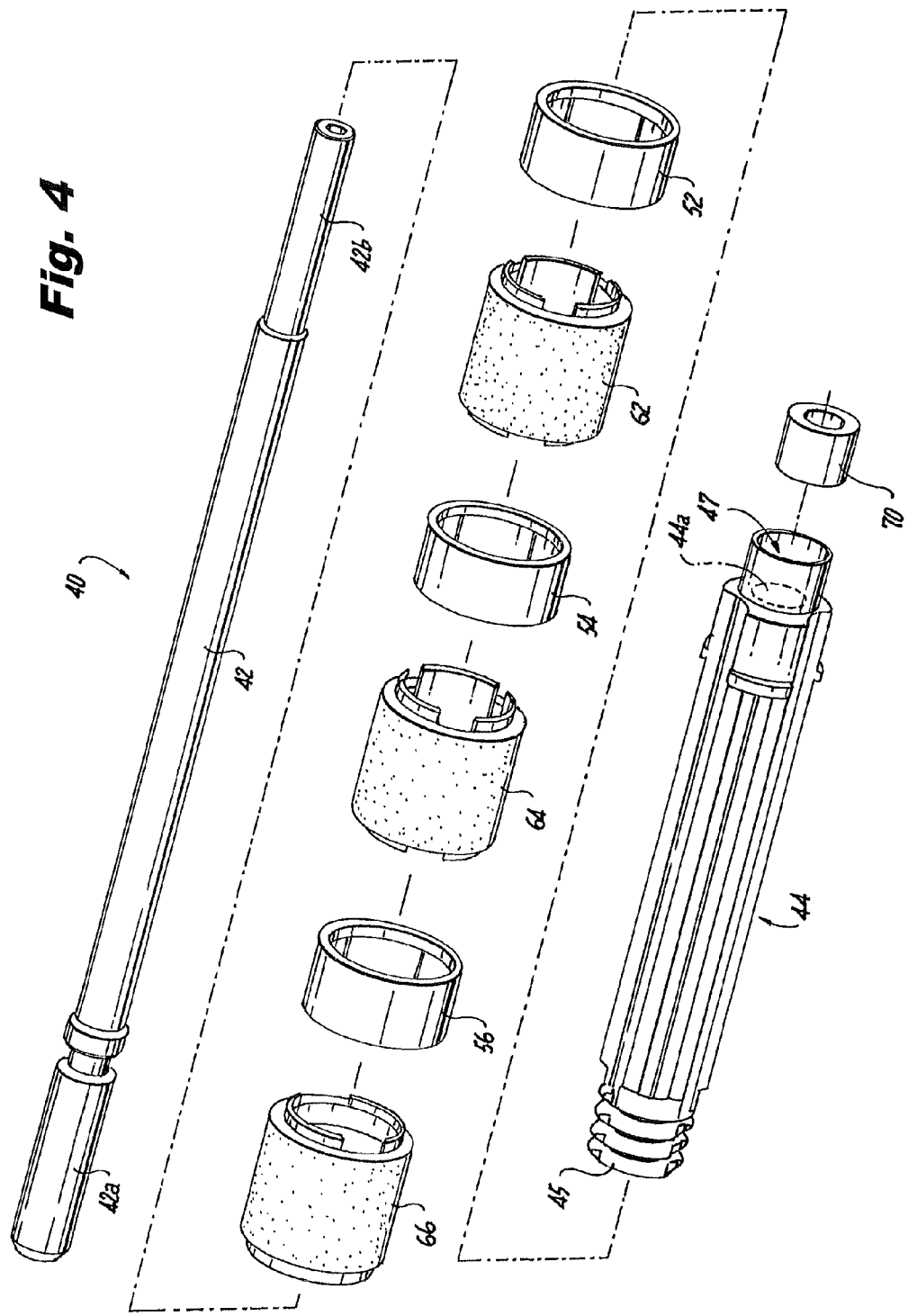
FIG. 4 is an exploded perspective view of the in-line quadripolar connector assembly of the subject invention with parts separated for ease of illustration.

Referring now to FIGS. 2-4, there is illustrated a proximal end portion of cardiac lead 10 which includes the in-line (IS-4 type) four pole connector assembly 40 at the proximal end of the lead body 12. The four-pole connector assembly 40 includes an elongated electrode pin 42 having opposed proximal and distal end portions 42a, 42b (see FIG. 4). The proximal end portion 42b of electrode pin 42 serves as one of the four electrodes of connector assembly 40 and is used to manually activate the fixation screw 14 (i.e., to extend and retract the screw), as discussed in more detail below.

The proximal end portion of the transmitting torque coil 30 is operatively connected to the distal end portion 42a of the electrode pin 42, as best seen in FIG. 2 This is preferably accomplished by welding the proximal end of coil 30 to the distal end portion 42a of electrode pin 42. Preferably, the coil 30 is covered by a heat shrink tube 48, as shown in FIG. 3, which acts to insulate and consolidate the torque transmitting coil 30.

Figure 5:
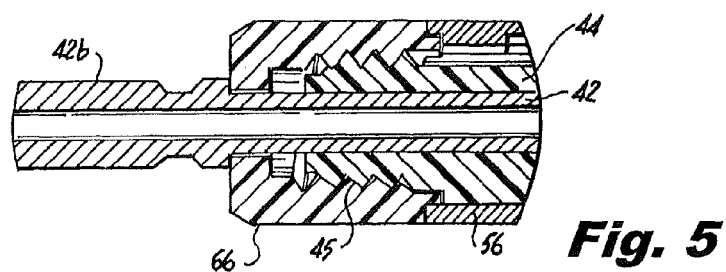
FIG. 5 is an enlarged cross-sectional view taken along line 5-5 of FIG. 2, showing the threaded connection between the inner support shaft and the proximal-most ring electrode of the connector assembly.

Referring to FIG. 4, in-line four-pole connector assembly 40 further includes an elongated inner support shaft 44 made from PEEK or a similar material and having a central bore 44a to accommodate electrode pin 42 in such a manner to support its rotation. The inner support shaft 44 is adapted and configured to support a stack of axially arranged annular electrodes 52, 54 and 56 and annular insulators 62, 64, and 66. The annular electrodes (52, 54 and 56) and annular insulators (62, 64 and 66) are mounted in fixed relationship to the inner support shaft 44, so that they will not rotate relative to the support shaft 44 when the electrode pin 42 is rotated to activate the fixation screw 14. As best seen in FIG. 5, the proximal-most annular insulator 66 is threadably engaged with a threaded proximal end portion 45 of the inner support shaft 44. This secures the other two electrodes and the three insulators in place on the inner support shaft 44 relative to the lead body 12.

Figure 6:
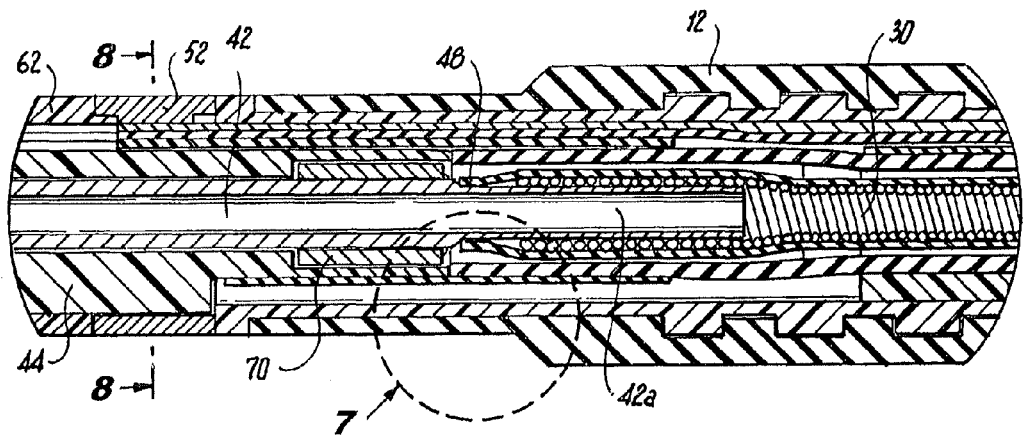
FIG. 6 is an enlarged cross-sectional view of the connector assembly of the cardiac lead of the subject invention corresponding to FIG. 2, showing the welded connection between the torque transmitting coil and the distal end portion of the rotatable pin electrode, as well as the welded connection between distal end portion of the electrode pin and the spacer hull
Figure 7:
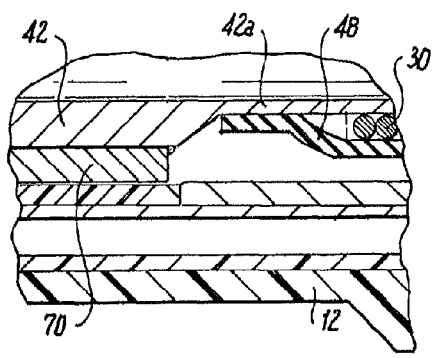
FIG. 7 is an enlarged localized view of the connector assembly at region 7 of FIG. 6.

Referring to FIG. 6, a cylindrical hull 70 is secured to the distal end portion 42a of electrode pin 42 and resides within a recess 47 formed in the support shaft 44, proximal to the connection of the electrode pin 42 and torque transmitting coil 30, to support rotation of the electrode pin 42 within the central bore 44a of support shaft 44. In essence, the hull 70 serves as a bearing to support the axial rotation of the electrode pin 42 relative to the support shaft 44. Preferably, hull 70 is welded or otherwise mechanically joined to the distal end portion 42a of electrode pin 42. As shown in FIG. 7, there is a sufficient running clearance between the outer diameter of the hull 70 and the inner diameter of the recess 47 in support shaft 44 to allow for the free rotation of hull 70 within recess 47.

Figure 8:
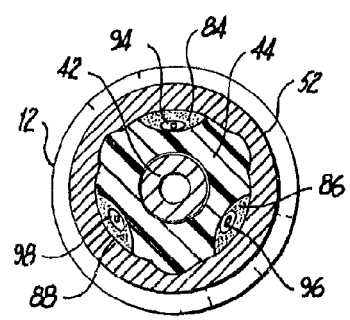
FIG. 8 is a cross-sectional view taken along line 8-8 of FIG. 6, illustrating the three circumferentially spaced apart side channels of the support shaft which accommodate conductive wires connecting the electrode rings of the connector assembly with the ring electrodes associated with the distal end portion of the lead.

Referring to FIG. 8, the elongated inner support shaft 44 includes circumferentially spaced apart side channels 84, 86 and 88. Each side channel is adapted and configured to accommodate a respective set of conductive wires 94, 96 and 98. These wires electrically connect the ring electrodes associated 22, 24 and 26 with the distal end portion of lead body 12 with the axially stacked annular electrodes 52, 54 and 56 of the connector assembly 40. The side channels are preferably backfilled with epoxy. The wire sets 94, 96 and 98 are preferably hulled at their ends to facilitate welding to the electrodes 52, 54 and 56.

In use, rotation of the proximal end portion 42b of electrode pin 42 relative to the inner support shaft 44 and the axially stacked electrodes (52, 54 and 56) and insulators (62, 64 and 66) of connector assembly 40, will cause the corresponding rotation of the torque transmitting conductor coil 30 within the interior bore of lead body 12. In response, the fixation screw 14 at the distal end of lead body 12 will rotate for extension and retraction.

While the subject invention has been described with respect to preferred and exemplary embodiments, those skilled in the art will readily appreciate that various changes and/or modifications can be made to the invention without departing from the spirit or scope of the invention as described herein. For example, those skilled in the art will appreciate that the quadripolar connector assembly, while described herein by way of a non-limiting example as a IS-4 type connector, could be a DF-4 type quadripolar connector, designed for defibrillation rather than pacing.

What is claimed is:

1. An implantable quadripolar cardiac lead comprising:
   a) an elongated lead body having opposed proximal and distal end portions and having an interior lumen extending therethrough;
   b) an axially rotatable retractable and extendable fixation helix operatively associated with the distal end portion of the lead body;
   c) an in-line quadripolar connector assembly operatively associated with the proximal end portion of the lead body and including an elongated rotatable pin electrode having opposed proximal and distal end portions; and
   d) an elongated torque transmitting conductor coil extending through the interior lumen of the lead body and having a proximal end portion connected to the distal end portion of the rotatable pin electrode and a distal end portion connected to the rotatable fixation helix, to facilitate manual activation of the fixation helix, wherein the fixation helix is electrically connected to the rotatable pin electrode, wherein the connector assembly includes an elongated inner support shaft supporting a stack of axially spaced apart electrode rings separated from one another by a corresponding plurality of axially spaced apart insulator rings, wherein each electrode ring of the connector assembly is in electrical communication with a corresponding ring electrode associated with the distal end portion of the lead body, wherein the inner support shaft is engaged to the stack of electrode rings for non-rotation of the electrode rings relative to the inner support shaft, and wherein the rotatable pin electrode is engaged for rotation relative to the inner support shaft for actuation of the fixation helix.

2. An implantable quadripolar cardiac lead as recited in claim 1, wherein the fixation helix is electrically connected to the elongated torque transmitting coil and the elongated torque transmitting coil is covered by a heat shrink tube.

3. An implantable quadripolar cardiac lead as recited in claim 1, wherein a proximal end portion of the rotatable pin electrode is one of four electrodes of the connector assembly.

4. An implantable quadripolar cardiac lead as recited in claim 1, wherein the quadripolar connector assembly includes a proximal-most insulator ring that is threadably engaged with a proximal end portion of the inner support shaft.

5. An implantable quadripolar cardiac lead as recited in claim 1, wherein a cylindrical hull is secured to the distal end portion of the pin electrode, proximal to the connection of the pin electrode and torque transmitting conductor coil, to support rotation of the pin electrode relative to the support shaft.

6. An implantable quadripolar cardiac lead as recited in claim 5, wherein the hull in accommodated for rotation within a recess formed in a distal end portion of the support shaft.

7. An implantable quadripolar cardiac lead as recited in claim 5, wherein the elongated support shaft includes three circumferentially spaced apart side channels, and wherein each side channel is adapted and configured to accommodate conductive wires communicating with at least one of the axially spaced apart electrode rings.

8. An implantable quadripolar cardiac lead comprising:
   a) an elongated lead body having opposed proximal and distal end portions and having an interior lumen extending therethrough;
   b) an electrically active axially rotatable fixation helix operatively associated with the distal end portion of the lead body;
   c) an in-line quadripolar connector assembly operatively associated with the proximal end portion of the lead body and including an elongated rotatable pin electrode having opposed proximal and distal end portions; and
   d) torque transmitting means extending through the interior lumen of the lead body, electrically connecting the rotatable pin electrode to the rotatable fixation helix, for facilitating manual rotation of the fixation helix, wherein the connector assembly includes an elongated inner support shaft supporting a stack of axially spaced apart electrode rings separated from one another by a corresponding plurality of axially spaced apart insulator rings, wherein each electrode ring of the connector assembly is in electrical communication with a corresponding ring electrode associated with the distal end portion of the lead body, wherein the inner support shaft is engaged to the stack of electrode rings for non-rotation of the electrode rings relative to the inner support shaft, and wherein the rotatable pin electrode is engaged for rotation relative to the inner support shaft for actuation of the fixation helix.

9. An implantable quadripolar cardiac lead as recited in claim 8, wherein the torque transmitting means comprises a helical coil.

10. An implantable quadripolar cardiac lead as recited in claim 9, wherein the helical coil is covered by a heat shrink tube.

11. An implantable quadripolar cardiac lead as recited in claim 9, wherein a proximal end portion of the rotatable pin electrode is one of four electrodes of the connector assembly.

12. An implantable quadripolar cardiac lead as recited in claim 11, wherein the quadripolar connector assembly includes a proximal-most insulator ring that is threadably engaged with a proximal end portion of the inner support shaft.

13. An implantable quadripolar cardiac lead as recited in claim 11, wherein a cylindrical hull is secured to the distal end portion of the pin electrode, proximal to the connection of the pin electrode and the coil, to support rotation of the pin electrode relative to the support shaft.

14. An implantable quadripolar cardiac lead as recited in claim 13, wherein the hull is accommodated for rotation within a recess formed in a distal end portion of the support shaft.

15. An implantable quadripolar cardiac lead as recited in claim 13, wherein the elongated support shaft includes three circumferentially spaced apart side channels, and wherein each side channel is adapted and configured to accommodate conductive wires communicating with at least one of the axially spaced apart electrode rings of the connector assembly.

16. An implantable quadripolar cardiac lead comprising:
   a) an elongated lead body having opposed proximal and distal end portions and having an interior lumen extending therethrough;
   b) an electrically active axially rotatable fixation helix and three axially spaced apart ring electrodes operatively associated with the distal end portion of the lead body;
   c) an in-line quadripolar connector assembly operatively associated with the proximal end portion of the lead body and including an elongated rotatable pin electrode having opposed proximal and distal end portions, and a stack of three axially spaced apart electrode rings separated from one another by a corresponding plurality of axially spaced apart insulator rings, wherein each electrode ring of the connector assembly is in electrical communication with a corresponding ring electrode; and
   d) an elongated torque transmitting conductor coil extending through the interior lumen of the lead body and having a proximal end portion connected to the distal end portion of the rotatable pin electrode and a distal end portion connected to the rotatable fixation helix, to facilitate manual activation of the fixation helix, wherein the connector assembly includes an elongated inner support shaft supporting the stack of axially spaced apart electrode rings separated from one another by a corresponding plurality of axially spaced apart insulator rings, wherein the inner support shaft is engaged to the stack of electrode rings for non-rotation of the electrode rings relative to the inner support shaft, and wherein the rotatable pin electrode is engaged for rotation relative to the inner support shaft for actuation of the fixation helix.

17. An implantable quadripolar cardiac lead as recited in claim 16, wherein the connector assembly includes a proximal-most insulator ring that is threadably engaged with a proximal end portion of the inner support shaft.

18. An implantable quadripolar cardiac lead as recited in claim 16, wherein a cylindrical hull is secured to the distal end portion of the pin electrode and is accommodated within a recess formed in the distal end portion of the support shaft, proximal to the connection of the pin electrode and the coil, to support rotation of the pin electrode relative to the support shaft.

* * * * *